US012150748B2

(12) United States Patent
Rheineck et al.

(10) Patent No.: US 12,150,748 B2
(45) Date of Patent: Nov. 26, 2024

(54) MRI RECEIVER COIL SYSTEM

(71) Applicant: MR Instruments, Inc., Minneapolis, MN (US)

(72) Inventors: Thomas Rheineck, Minneapolis, MN (US); Lawrence Tanenbaum, Riverside, CT (US); Mark Jensen, Hopkins, MN (US); Michael Lancial, Saint Louis Park, MN (US); Grant Thompson, Saint Paul, MN (US); Leon Ricord, Waconia, MN (US); Juan Martinez, Houlton, WI (US); Robert Bushey, Coon Rapids, MN (US); Brian Fabian, Shakopee, MN (US); Khai Tran, Chanhassen, MN (US)

(73) Assignee: MR Instruments, Inc., Minneapolis, MN (US)

( * ) Notice: Subject to any disclaimer, the term of this patent is extended or adjusted under 35 U.S.C. 154(b) by 81 days.

(21) Appl. No.: 17/756,280

(22) PCT Filed: Nov. 27, 2020

(86) PCT No.: PCT/US2020/062511
§ 371 (c)(1),
(2) Date: May 20, 2022

(87) PCT Pub. No.: WO2021/108773
PCT Pub. Date: Jun. 3, 2021

(65) Prior Publication Data
US 2022/0409085 A1     Dec. 29, 2022

Related U.S. Application Data

(60) Provisional application No. 62/940,435, filed on Nov. 26, 2019.

(51) Int. Cl.
  *A61B 5/055*   (2006.01)
  *G01R 33/34*   (2006.01)
  *G01R 33/36*   (2006.01)

(52) U.S. Cl.
  CPC ........ *A61B 5/055* (2013.01); *G01R 33/34007* (2013.01); *G01R 33/36* (2013.01); *G01R 33/34084* (2013.01)

(58) Field of Classification Search
  CPC .. A61B 5/055; G01R 33/34007; G01R 33/36; G01R 33/34084; G01R 33/4814; G01R 33/3415
  See application file for complete search history.

(56) References Cited

U.S. PATENT DOCUMENTS

| 6,155,974 A | 12/2000 | Fish |
| 6,163,240 A | 12/2000 | Zuk et al. |

(Continued)

FOREIGN PATENT DOCUMENTS

| CA | 3097828 A1 | 10/2019 |
| CN | 107773241 | 3/2018 |

(Continued)

OTHER PUBLICATIONS

"U.S. Appl. No. 16/617,350, Examiner Interview Summary mailed Oct. 13, 2022", 2 pgs.

(Continued)

*Primary Examiner* — Peter Luong
(74) *Attorney, Agent, or Firm* — Schwegman Lundberg & Woessner, P.A.

(57) ABSTRACT

A wearable, open and pliable conforming MRI receiver coil system having an assembly of MRI imaging coils, each configured in a framework to simultaneously apply or position MRI receiver antennae and medical implements such as ultrasound transducers against the skull or skin of a patient.

(Continued)

The system is configured to perform an MRI imaging and operation of the one or more medical implements simultaneously.

20 Claims, 10 Drawing Sheets

(56) References Cited

U.S. PATENT DOCUMENTS

| | | | |
|---|---|---|---|
| 7,345,483 | B2 | 3/2008 | Vaughan |
| 7,619,413 | B2 | 11/2009 | Wiggins |
| 7,887,488 | B2 | 2/2011 | Masters |
| 8,406,853 | B2 | 3/2013 | Petropoulos |
| 8,487,615 | B2 | 7/2013 | Zhu et al. |
| 8,570,037 | B2 | 10/2013 | Schellekens et al. |
| 8,604,789 | B2 | 12/2013 | Shvartsberg et al. |
| 8,797,029 | B2 | 8/2014 | Zhu et al. |
| 8,952,694 | B2 | 2/2015 | Biber et al. |
| 9,204,818 | B2 | 12/2015 | Moffatt |
| 9,554,779 | B2 | 1/2017 | Larson et al. |
| 9,958,517 | B2 | 5/2018 | Biber et al. |
| 10,765,403 | B2 | 9/2020 | Tretbar et al. |
| 10,827,948 | B1 | 11/2020 | Tramm et al. |
| 10,895,615 | B2 | 1/2021 | Wynn et al. |
| 11,839,447 | B2 | 12/2023 | Rheineck et al. |
| 2008/0007259 | A1 | 1/2008 | Driemel |
| 2008/0306377 | A1 | 12/2008 | Piron et al. |
| 2009/0227852 | A1 | 9/2009 | Glaser |
| 2010/0296723 | A1 | 11/2010 | Greer et al. |
| 2010/0312093 | A1 | 12/2010 | Biglieri et al. |
| 2012/0062233 | A1 | 3/2012 | Reykowski |
| 2012/0112748 | A1 | 5/2012 | Hetherington et al. |
| 2012/0265052 | A1 | 10/2012 | Rohr et al. |
| 2012/0265053 | A1 | 10/2012 | Rohr et al. |
| 2013/0317346 | A1 | 11/2013 | Alagappan et al. |
| 2014/0213886 | A1 | 7/2014 | Menon et al. |
| 2015/0112187 | A1 | 4/2015 | Petropoulos et al. |
| 2015/0265365 | A1 | 9/2015 | Andrews et al. |
| 2015/0265366 | A1 | 9/2015 | Andrews et al. |
| 2015/0265857 | A1 | 9/2015 | Barnes et al. |
| 2016/0062233 | A1 | 3/2016 | Masuyama et al. |
| 2016/0256713 | A1 | 9/2016 | Saunders et al. |
| 2016/0291100 | A1 | 10/2016 | Ha et al. |
| 2016/0354175 | A1 | 12/2016 | Andrews et al. |
| 2017/0209070 | A1 | 7/2017 | Rohr et al. |
| 2017/0248666 | A1 | 8/2017 | Rothgang et al. |
| 2017/0296289 | A1 | 10/2017 | Andrews et al. |
| 2018/0070852 | A1 | 3/2018 | Azulay et al. |
| 2018/0310894 | A1 | 11/2018 | Gallant et al. |
| 2019/0154774 | A1 | 5/2019 | Hushek et al. |
| 2021/0121066 | A1 | 4/2021 | Rheineck et al. |
| 2023/0380690 | A1 | 11/2023 | Rheineck et al. |

FOREIGN PATENT DOCUMENTS

| | | |
|---|---|---|
| EP | 3721245 A1 | 10/2020 |
| WO | WO-2017143444 A1 | 8/2017 |
| WO | WO-2019209389 A1 | 10/2019 |
| WO | WO-2021108773 A1 | 6/2021 |

OTHER PUBLICATIONS

"U.S. Appl. No. 16/617,350, Final Office Action mailed Jun. 24, 2022", 31 pgs.
"U.S. Appl. No. 16/617,350, Response filed Dec. 20, 2022 to Final Office Action mailed Jun. 24, 2022", 14 pgs.
"Chinese Application Serial No. 202090000996.5, Notification to Make Rectification mailed Jun. 20, 2022", with machine translation, 3 pgs.
"Chinese Application Serial No. 202090000996.5, Response filed Oct. 20, 2022", with machine translation, 18 pgs.
"International Application Serial No. PCT/US2019/013639, International Preliminary Report on Patentability mailed Nov. 5, 2020", 8 pgs.
"International Application Serial No. PCT/US2019/013639, International Search Report mailed Apr. 4, 2019", 2 pgs.
"International Application Serial No. PCT/US2019/013639, Written Opinion mailed Apr. 4, 2019", 6 pgs.
"International Application Serial No. PCT/US2020/062511, International Preliminary Report on Patentability mailed Jun. 9, 2022", 7 pgs.
"U.S. Appl. No. 16/617,350, Non Final Office Action mailed Feb. 15, 2022", 21 pgs.
"U.S. Appl. No. 16/617,350, Response filed May 16, 2022 to Non Final Office Action mailed Feb. 15, 2022", 14 pgs.
"European Application Serial No. 19792180.2, Extended European Search Report mailed Jul. 2, 2021", 11 pgs.
"European Application Serial No. 19792180.2, Response filed Jan. 27, 2022 to Extended European Search Report mailed Jul. 2, 2021", 12 pgs.
"International Application Serial No. PCT/US2020/062511, International Search Report mailed Feb. 26, 2021", 2 pgs.
"International Application Serial No. PCT/US2020/062511, Written Opinion mailed Feb. 26, 2021", 5 pgs.
Fabian, Kording, et al., "Evaluation of a Portable Doppler Ultrasound Gating Device for fetal Cardiac MR Imaging: Initial Results at 1.5T and 3T", Magn Reson Med Sci 2018; 17, (2018), 308-317.
Harvey, Paul R., et al., "MultiTransmit parallel RFtransmission technology", (Aug. 10, 2010), 16 pgs.
Zhou, Anqi, "RF Coils in MRI", (May 19, 2006), 33 pgs.
"U.S. Appl. No. 16/617,350, Supplemental Notice of Allowability mailed Aug. 16, 2023", 4 pgs.
"European Application Serial No. 20892846.5, Extended European Search Report mailed Nov. 7, 2023", 11 pgs.
"U.S. Appl. No. 16/617,350, Non Final Office Action mailed Jan. 19, 2023", 36 pgs.
"Chinese Application Serial No. 202090000996.5, Office Action mailed Jan. 9, 2023", w English Translation, 4 pgs.
"European Application Serial No. 20892846.5, Response to Communication pursuant to Rules 161(2) and 162 EPC filed Dec. 28, 2022", 11 pgs.
"Chinese Application Serial No. 202090000996.5, Response filed Mar. 1, 2023 to Office Action mailed Jan. 9, 2023", w English claims, 19 pgs.
"Chinese Application Serial No. 202090000996.5, Notification to Make Rectification mailed Mar. 14, 2023", with machine translation, 5 pgs.
"U.S. Appl. No. 16/617,350, Response filed Apr. 18, 2023 to Non Final Office Action mailed Jan. 19, 2023", 13 pgs.
"Chinese Application Serial No. 202090000996.5, Response filed May 23, 2023 to Notification to Make Rectification mailed Mar. 14, 2023", w English claims, 28 pgs.
"U.S. Appl. No. 16/617,350, Notice of Allowance mailed Aug. 2, 2023", 13 pgs.
"U.S. Appl. No. 18/366,525, Non Final Office Action mailed Mar. 13, 2024", 26 pgs.
"U.S. Appl. No. 18/366,525, Response filed May 10, 2024 to Non Final Office Action mailed Mar. 13, 2024", 8 pgs.
"European Application Serial No. 19792180.2, Communication Pursuant to Article 94(3) EPC mailed Feb. 13, 2024", 9 pgs.
"U.S. Appl. No. 18/366,525, Notice of Allowance mailed Jun. 4, 2024", 8 pgs.
"European Application Serial No. 19792180.2, Response filed Jun. 24, 2024 to Communication Pursuant to Article 94(3) EPC mailed Feb. 13, 2024", w claims, 11 pgs.
"U.S. Appl. No. 18/366,525, Supplemental Notice of Allowability mailed Jul. 10, 24", 4 pgs.
"European Application Serial No. 20892846.5, Response filed May 21, 2024 to Extended European Search Report mailed Nov. 7, 2023", w claims, 13 pgs.

MRI RECEIVER COIL SYSTEM

PRIORITY

This patent application is a U.S. national stage filing under 35 U.S.C. § 371 from International Application No. PCT/US2020/062511, filed on Nov. 27, 2020, and published as WO2021/108773 on Jun. 3, 2021, which claims priority to U.S. Provisional Patent Application No. 62/940,435, filed on Nov. 26, 2019, the benefit of priority of each of which is claimed herein, and which applications and publication are hereby incorporated herein by reference in their entirety.

FIELD

The present invention is directed to an open and conformable magnetic resonance imaging ("MRI") receiver coil system that is capable of supporting ultrasound transducers, diagnostic, therapeutic, and interventional implements, devices, systems, and assemblies. More particularly, the present invention is directed to a MRI receiver coil system capable of positioning MRI antenna receiver coils flush against the skull or skin of a patient while also supporting and or allowing the positioning of ultrasound transducers, diagnostic, therapeutic, and interventional implements generally flush against a patient's skull or skin.

BACKGROUND

During the 1970s and 1980s, numerous advancements in medical imaging were made that enabled physicians to better examine and diagnose patients. One such advancement was the magnetic resonance imaging, or MRI device. MRIs permitted physicians to use magnetic fields and radio waves to capture high quality images of internal tissue without having to do exploratory surgery, or exposing patients to high levels of radiation.

Although an MRI can be used to examine the brain, organs, glands, and soft tissues of patients, it has been particularly useful for scanning the head or cranium of patients. An MRI scan is able to render high quality images of the brain and cranial structures. Physicians are able to use an MRI to see abnormalities such as brain bleeding and swelling, aneurysms, stroke, tumors, as well as upper cervical spine injuries and disorders.

Once an abnormality or injury is identified and located, it is possible to use an MRI to support the treatment of patients. For instance, in brain abnormalities, a surgeon may use an MRI while conducting neurosurgery-intervention (e.g., deep brain stimulation ("DBS"), laser ablation, Focus Ultrasound Ablation (or neurosurgery), and the like—known as MR-guided neurotherapy or MR-guided neurosurgery. The ability to use MR-guided neurotherapy significantly increases visibility to the treatment area and improves the outcome of the surgery.

Using an MRI during neurosurgery, however, presents some significant challenges. First, conventional head coils, as illustrated in FIG. 1A, tend to be large rigid structures that fit over a patient's head like an enclosed birdcage, making access virtually impossible. Second, the large rigid head coils make head stabilization, which is critical during neurosurgery, more difficult. During a neurosurgical procedure, a patient's head is held or fixed by a rigid, non-magnetic head frame or holder that is connected to, but spaced apart from, a patient's head. These head holders typically comprise a circular or rectangular frame with pins or screws that are drilled or driven into the patient's head to hold it still. The combination of the head frame with the rigid head coil compounds the difficulty of accessing a particular cranial surgery or therapy site. Additionally, the rigid head coils further add to the claustrophobia experienced by some patients positioned in the enclosed birdcage during routine diagnostic procedures.

In instances where a rigid head coil and head holder cannot be used together, generally flat or semi-flexible surface coils are used to obtain the MRI images. The flat surface coils are designed to be placed as close as possible to the patient's head in order to increase the signal-to-noise ratio. These flat surface coils, while somewhat pliable, are not generally conforming to a patient's head. This lack of pliability, along with the stabilization head frame, results in the distance between the surface coil and the patient's cranium or head to be increased, thereby having a negative impact on the signal-to-noise ratio, and resultingly degrading the image quality.

In MR-guided neurotherapy or neurosurgery, there is a need to have one or more head coils or surface coils that can be comfortably worn by, or placed on, a patient to have a generally consistent, strong, and uniform sign-to-noise ratio. There is also a need to have a comfortable head coil or surface coil that has an adjustable open framework that provides physicians and surgeons with greatly improved access to the patient such that diagnostic, therapeutic and interventional devices ("scanning and surgical accessory devices"), like ultrasound transducers, cannula guides, electroencephalography EEG, electromyography EMG, or electronystagmography ENG sensors can be placed flush against a patient's head or body while still providing improved access to a surgical site.

Conventional rigid and partially open framework MRI head coils have limited space in which to insert diagnostic, therapeutic and interventional devices or scanning or surgical accessory devices, like ultrasound transducers, cannula guides, electroencephalography EEG, electromyography EMG, or electronystagmography ENG sensors. During surgery, a surgical assist or another surgeon is often tasked with holding the scanning or surgical accessory devices in place while the surgery is being conducted or during a break in surgery where additional images may be acquired. A need exists to have an MRI head coil that is able to support one or more scanning or surgical accessory devices.

Another need exists to have an MRI head coil that is able to position MRI imaging coils and diagnostic, therapeutic and interventional devices generally flush to or proximate to the patient's skin. Still another need exists to have an MRI head coil that includes MRI imaging coils placed about one or more diagnostic, therapeutic and interventional devices such that MRI imaging and diagnostic, therapeutic and interventional examination can be simultaneously or individually conducted. Still another need exists to have an MRI head coil that has one or more scanning or surgical accessory device supports that positions the scanning or surgical accessory devices against or proximate to the patient's skin and proximate to MRI imaging coils.

Still another need exists to have a comfortable head or surface coil that has an open framework and/or is adjustable to permit improved access for placement of a head fixation frame or holder. Another need exists to have a comfortable head or surface coil that is adjustable such that it has at least one access panel or openings that can be moved or displaced to provide surgical or therapy site access. Additionally, another need also exists to have a comfortable head coil or surface coil that eliminates or greatly reduces patient claustrophobia for diagnostic exams where the patient is awake.

Yet another need exists to place multiple, pliable surface coils on the head, or on any anatomy, wherein multiple coils can be arranged to maximize the SNR (image quality) as well as the interventional access.

SUMMARY

The present invention is directed to an open, conformable MRI receiver coil system whose receiver antennae can be positioned generally flush with the patient's body or skull while it is also able to simultaneously support and/or accommodate one or more different ultrasound transducers, diagnostic, therapeutic, and/or interventional devices or therapy implements, which also are generally flush with the skull or body. This simultaneity of both MRI receiver antennae and ultrasound transducers or other diagnostic and therapeutic implements being generally flush with the skull or body while performing their respective functions is novel.

In one aspect of the invention, the open and conformable MRI coil receiver system includes one or more MRI coils, including but not limited to a head coil, neck coil, spine coil, extremity coil, surface coil, or body coil. The MRI coil receiver system is able to be coupled to and communicate with at least a magnetic resonance ("MR") system. It is also contemplated herein that the MRI receiver coil system of the present invention is able to be coupled to and communicate with various other systems such as ultrasound systems, diagnostic systems, therapeutic systems, and/or interventional systems. The MRI receiver coil system is able to communicate with the various systems simultaneously, thereby reducing or eliminating the need to interrupt an ongoing procedure.

In another aspect of the invention, placing or positioning the MRI receiver antenna and one or more of the ultrasound transducers, diagnostic, therapeutic, interventional implements simultaneously flush against the patient's skull or skin, allows the capturing of high resolution images with minimal to no scattering that is common with conventional MRI imaging devices and systems.

In a related aspect of the invention, the open and conformable aspect of the MRI coils, of the MRI coil receiver system, create an open framework that allows for easier access to a patient's skull or skin. The open framework is created by a plurality of interconnected primary and secondary support members that form the MRI coil. Each of the primary support members contain one or more receiver antenna. Similarly, while not required, one or more of the second support members can contain one or more MRI receiver antenna. The primary support members are arranged or interconnected to form a variety of shapes or configurations such as a helmet or birdcage, or a surface coil. Any shape and configuration of the MRI coil is contemplated herein.

The configuration of the primary and secondary support members enable the receiver antenna and the ultrasound transducers, diagnostic, therapeutic, and/or interventional devices or therapy implements to be placed flush with the skull or skin of the patient. In one example embodiment of the invention, the secondary support members are configured to receive and position one or more of the ultrasound transducers, diagnostic, therapeutic, and/or interventional implements flush against the skull or skin of the patient while the receiver antenna are similarly positioned flush against the skull or skin of the patient. An additional advantage of the present invention is ability of the receiver antenna and the ultrasound transducers, diagnostic, therapeutic, and/or interventional devices or therapy implements to be positioned generally on the same plane while simultaneously performing their functions.

The MRI coil of the present invention is constructed of a material that allows it to conform to a patient's anatomy. By conforming to the patient's anatomy, it is able to place the receiver antenna and the ultrasound transducers, diagnostic, therapeutic, and/or interventional devices or therapy implements generally flush against the skull or skin of the patient. The MRI coil may be manufactured from a compressible material that is generally soft and comfortable when worn by a patient. The compressibility of the MRI coil is particularly important when it is positioned between a patient and a table. For instance, when a patient is laying upon an MRI table. Conventional MRI coils, unlike the present invention, are bulky and rigid causing patient discomfort.

The MRI coil of the present invention can also be manufactured from a material that has elastic, flexible, or resilient properties. An elastic material permits the MRI coil it to be adjustable in at least a lengthwise orientation. This adjustability enables the MRI coil to accommodate patients of varying sizes and shapes. It also permits a healthcare work to adjust, move or reposition as needed. Any one or a combination of materials may be used during construction to provide different properties or characteristics.

It is also contemplated herein that the MRI coil of the present invention can have portions, segments, or areas with varying physical properties. For instance, one portion of the imaging support appliance can be compressible while another portion may be elastic. Any combination of physical properties are contemplated herein, including but not limited to soft and hard, flexible and rigid, expandable and compressible, stretchable and retractable.

An advantage of the present invention is that the MRI coil has an open framework that provides virtually unlimited access to the patient's body. This is particularly important for cranial procedures where multiple devices need to be located in a relatively small space or area. The open framework provides access to surgical sites, placement of imaging devices, placement of therapeutic navigational guides, or other medical devices and peripheral equipment ("scanning, surgical and therapeutic accessory devices"). The open framework of the MRI coil permits scanning, surgical and therapeutic accessory devices such as ultrasound transducers to be supported and placed flush against the skull or skin of the patient.

In another example embodiment of the present invention, the MRI coil of the MRI receiver coil system is adjustable or reconfigurable. In this example embodiment, one or more of the primary or secondary support members may be removable, added to, or reconfigured with respect to the overall configuration of the MRI coil. The ability to reconfigure the MRI coil increases its versatility and allows it to be used in a wide variety of surgical and therapeutic procedures.

The MRI coil can also include one or more sensors that are either permanently connected to or removably connectable to a portion of the MRI coil. In one example embodiment, the sensors can be coupled to one or more of the primary and/or secondary support members. The sensors can be any desired sensor including but not limited to sensor to measure electroencephalography EEG, electromyography EMG, electronystagmography ENG readings, and the like.

The MRI coil includes one or more communication pathways that permits receipt and delivery of data between the MRI coil, ultrasound transducers, and/or sensors and other devices or systems such as an MRI scanner. The communication pathway may be physical, such as by one or more wires or it can be wireless through any number of wireless protocols such as WI-FI or Bluetooth™. The MRI receiver coil system can include an interface or hub that has a plurality sockets or connectors capable of receiving one or more of the receiver antenna and ultrasound, diagnostic, therapeutic, and/or interventional devices or therapy implements.

The above summary is not intended to limit the scope of the invention, or describe each embodiment, aspect, implementation, feature, or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore, and those to be commented on hereinafter, may be used not only in the specified combinations, but also in other combinations or in isolation, without departing from the scope of the present invention.

Figure 1A:
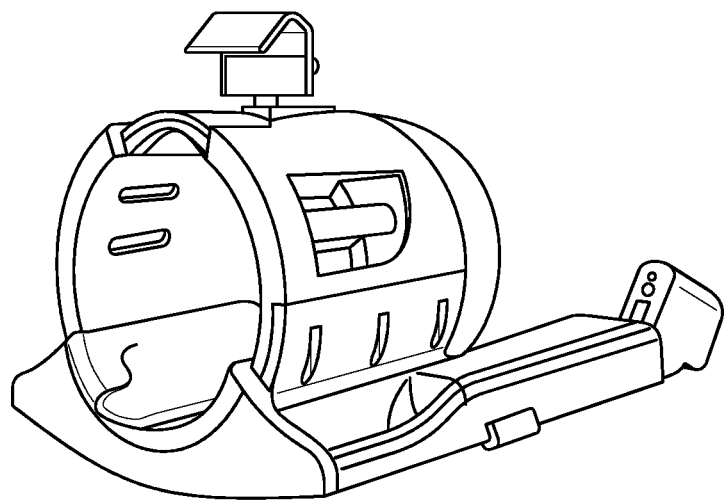
FIG. 1A is a perspective view of a conventional rigid non-wearable head coil.
Figure 1B:
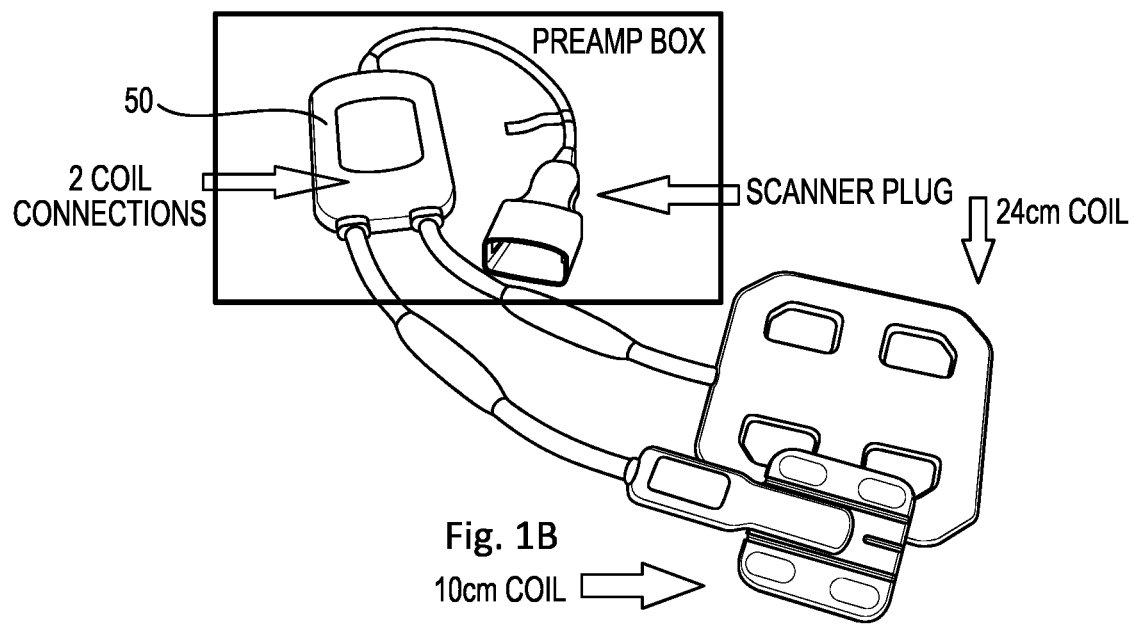
FIG. 1B is a perspective view of a preamp (signal amplifier) assembly that can be used with the wearable open and adjustable MRI receiver coil system of the present invention.

While the invention is amenable to various modifications and alternative forms, specifics thereof have been shown by way of example in the drawings and will be described in detail. It should be understood, however, that the intention is not to limit the invention to the particular example embodiments described. To the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration, rather than to limit the present invention.

Dimensions and relative proportions of components are merely provided as examples and can be varied unless specifically limited in a given claim. Thus, the dimensions and proportions can vary without departing from the scope of the invention.

As illustrated in FIGS. 2A-10B, the present invention comprises an open and conformable, Magnetic Resonance Imaging ("MRI") receiver coil system 10 that positions one or more MRI receiver antennae 40 flush against the skull or skin of a patient. The MRI receiver coil system 10 includes one or more MRI coils 12 that can take any number of shapes and configurations. As particularly, illustrated in FIG. 2A, the MRI coil 12 comprises a soft and pliable MRI head coil. This particular configuration of the MRI coil 12 can be form fitting to a patient's head and is able to fit approximately 100% of the population.

A unique feature of the MRI coil 12 is that it is able to position the MRI receiver antennae 40 proximate to or, ideally, flush against the skull or skin of the patient. While a MRI head coil is shown and described, it should be appreciated that the MRI coil 12 of the MRI receiver coil system 10 can be a surface coil, neck coil, spine coil, extremity coil, breast coil or any MRI coil that is placed on any anatomical location of a patient.

The MRI receiver coil system 10 is connectable to, and in communication with, other medical devices/equipment, such as a Magnetic Resonance Imaging ("MRI") scanner that is used for scanning a patient or subject. In order to capture the imaging, the MRI receiver antennae or imaging coils 40 receive radio frequency signals from the patient and then transmits the signals to a connected MRI control system of the scanner for image processing. As will be described in more detail, the MRI receiver antennae or imaging coils 40 can be fixed, removably attached to, or otherwise disposed within or about portions of a framework 20 of the MRI coil 12.

Using the MRI head coil of FIGS. 2A-7 as an exemplary embodiment, it can be seen that the MRI coil 12 of the present invention comprises an open and pliable framework 20 of interconnected struts that can be comfortably worn on a patient's head. The open framework 20 or struts comprise a plurality of interconnected primary frame or support members 20a that can be arranged to conform to a particular anatomical location or feature, such as a patient's head. The framework 20 can also include one or more medical implement or secondary support or frame members 21 arranged in an open framework. The primary support members 20a and secondary medical implement or support members 21 can be arranged or oriented in a variety of configurations that is only limited by the needs of the patient and the medical procedure to be performed. The primary support members 20a and the secondary support members 21 can have generally vertical, horizontal, and/or angular axes when compared to a long axis of a patient.

The secondary support members 21 can be formed with or connected to portions of the primary support members 20a such that they span openings formed by the interconnected primary support members 20a of the framework 20. The openings created by the primary and secondary support members, 20a and 21 respectively, can include but are not limited to a superior and inferior openings, anterior and posterior openings, and medial and lateral openings. The openings can be formed during the manufacturing process to define access sites corresponding to important anatomy and anatomical locations. The framework 20 of the MRI coil 12 can have any number and shape of openings.

The MRI radio frequency ("RF") imaging or receiver antenna coils 40 of the present invention are generally associated with at least one or more of the primary support members 20a of the MRI coil 12. Each of the primary support members 20a can have one or more MRI receiver antennae coils 40 that are used in conjunction with a MRI scanner that generates radio frequencies read by the MRI receiver antennae or coils 40. In one embodiment of the present invention, MRI receiver antennae 40 are also associated with one or more of the medical implement or secondary support members 21.

In an example embodiment of the present invention, the MRI receiver antennae 40 extend along at least a portion of a length of each of the primary support members 20a and, when present, one or more of the secondary support members 21. In other example embodiments of the present invention, there are multiple MRI receiver antennae 40 positioned along a length or thickness of each of the primary and secondary support members, 20a and 21 respectively. In yet another embodiment of the invention, all or less than all of the primary and secondary support members, 20a and 21 respectively, include one or more MRI receiver antennae 40.

The present invention contemplates a number of embodiments having MRI receiver antennae 40 located in various locations on or within the various MRI coils 12 employed with the MRI receiver coil system 10. In one embodiment of the invention, for example, the MRI receiver antennae 40 are supported on or mounted to an inner surface of the primary support members 20a and one or more of the secondary support members 21 such that the MRI receiver antennae 40 are positioned generally between the patient's skull or skin, and the primary and secondary support members, 20a and 21, respectively. In this location the MRI receiver antennae 40 are generally kept flush against the skull or skin of the patient by the framework 20. The MRI receiver antennae 40 can be coupled to the primary support members 20a and the secondary support members 21 by any mechanical or chemical means known to one skilled in the art.

In another embodiment of the present invention, the MRI receiver antennae 40 can be positioned or disposed in one or more elongate channels or grooves extending into the inner surface of the primary and/or secondary support members 20a and 21, respectively. The MRI receiver antennae 40 can be fixed or removable from the channels. Additionally, the MRI receiver antennae can be held in the channels by being pressure-fitted or held by a mechanical or chemical means known to one skilled in the art.

In still another embodiment of the invention, the MRI receiver antennae 40 are enclosed or contained within an interior of one or more of the primary support members 20a and/or one or more of the secondary support members 21. While not required, a distance between a MRI receiver antenna 40 and the inner surface of a primary support member 20a or a secondary support member 21 can be predetermined during manufacturing such that when the MRI coil 12 is worn by or placed on a patient the MRI receiver antennae 40 are placed and held generally flush against the patient's skull or skin.

Since the MRI coil 12 and its framework 20 can be constructed of a compressible material for comfort and pliability, any change in distance between the MRI antennae 40 and the skin or skull of a patient is important when the MRI antennae 40 are encased within the MRI coil 12. The present invention takes into account any changes in distances during the manufacturing process to ensure that the MRI receiver antennae 40 are positioned generally proximate to or flush against a patient's skull or skin when the MRI coil 12 is being worn or used. Unlike conventional MRI head coils, the MRI coils 12 of the present invention are comfortable, open, adjustable, pliable, and importantly, may be comfortably worn flush against a patient's skull or skin.

Another unique aspect of the present invention is its ability to simultaneously support and/or accommodate one or more different ultrasound, diagnostic, therapeutic, and/or interventional devices or therapy implements along with the MRI receiver antennae 40. The MRI coil 12 is uniquely configured to simultaneously position and hold the MRI receiver antennae 40 and one or more of the different ultrasound, diagnostic, therapeutic, and/or interventional devices or therapy implements proximate to or flush against the skull or skin of a patient.

One of the unique configurations of the MRI coils 12 of the present invention, is that one or more of the secondary support members 21 has a size and/or shape that is able to receive and, at least temporarily, hold one or more diagnostic, therapeutic, and interventional devices such as ultrasound transducers, drills, cannulas, and other sensors and medical devices such as electroencephalography EEG, electromyography EMG, or electronystagmography ENG sensors flush against the skull or skin of a patient. Hereinafter, these devices or implements will be referred to as "diagnostic and surgical accessories" 60. As mentioned above, the framework 20 of the MRI coils 12 is able to simultaneously position and hold the diagnostic and surgical accessories 60 and MRI receiver antennae 40 flush against or proximate to the patient's skull or skin.

As briefly mentioned above, one or more of the secondary or medical implement support members 21 is able to accommodate one or more of the MRI receiver antennae 40. By combining MRI receiver antennae 40 in at least a portion of the secondary support members 21, along with the diagnostic and surgical accessories 60, a healthcare worker is able selectively or simultaneously obtain MRI imaging during diagnostic, therapeutic, and interventional device procedures. The versatility of the present invention provides healthcare workers with real-time high-resolution anatomical visualization during procedures.

While the framework 20 is flush with the patient's body or head, the open and adjustable characteristics of the framework 20 enables diagnostic and surgical accessories, not coupled to the secondary support members 21, to also be placed or positioned flush against the patient's body or skull. The ability to have some diagnostic and surgical accessories 60 coupled to the secondary support members 21, while others are uncoupled, allows for even greater versatility in the ability to provide diagnostic, therapeutic, and interventional procedures while the patient wears the MRI coil 12, such as a MRI head coil.

Conventional MRI coils, especially MRI head coils or birdcages, are rigid and uncomfortable. The unique composition of some embodiments of present invention provide patients with a more comfortable and enjoyable experience. In these example embodiments, the primary support members 20a and/or the secondary support members 21 of the framework 20 comprise an open or closed cell foam material. The foam material is generally flexible and compressible to promote comfort and to allow it to be moved or adjusted during scanning/imaging. The flexible and compressibility of the framework 20 also allows it to be adjusted or moved during therapeutic or interventional procedures. Any material that provides cushioning, while also being flexible, may be used and should be considered to be within the spirit and scope of the invention.

In yet another example embodiment of the present invention, the framework 20 of the MRI coil 12 may comprise any material(s) that encases or supports the MRI receiver antennae 40. For example, the framework 20 may comprise a generally thin and flexible substrate or band that can be bent and/or stretched to conform to a patient's head or body. The band configuration of the framework 20, and its adjustability, enables the MRI receiver antenna 40 and the other diagnostic and surgical accessories 60 to simultaneously be placed flush with the patient's skull or skin.

In one embodiment of the invention, the material is manufactured from a closed cell structure such that can be sterilized by conventional sterilization processes to permit repeated use of the framework 20 of the MRI coil 12. In another example embodiment of the invention, the MRI coil 12 is designed such that it is easily disconnected from the MRI system and other systems used with ancillary diagnostic and surgical accessories 60. Further, the MRI coil 12 may be manufactured from materials that are recyclable. The unique designs and materials of the present invention enable the MRI coil 12 to be a single-use medical device item. The ability to disconnect and recycle a single-use MRI coil 12 is especially advantageous when it is used during interventional surgical procedures as it eliminates the requirement of, and cost associated with, sterilization.

As illustrated in the various figures, and as described in greater detail below, the framework 20 of the MRI coil 12 may have a shape or configuration that can be placed upon, or worn by, a patient during scanning, surgical, and/or therapeutic procedures. The holes or openings created by the open framework 20 of the MRI coil 12 act as ventilation or access openings for access to the patient's body or head. These openings also provide access for head holders or head fixation frames that include pins and/or clamps that contact the patient's head in order to stabilize it during an interventional procedure, such as cranial surgery. The openness and flexibility of the framework 20 enables surgeons and hospital staff to select the ideal location for securing the head holder to the patient's head and provides a preferred option for nearly every patient head shape and size.

The openness and flexibility created by the openings of the framework 20 of the various embodiments also provides a surgeon and surgery staff with access to surgical or therapy sites. The openings may be shaped and sized such that they are capable of accommodating medical devices, such as an ultrasound transducer (such as, for example, low intensity focus ultrasound ("LIFU") or high intensity focus ultrasound ("HIFU"). The framework 20 may also support other types of medical devices used during therapy, surgical, and other interventional procedures, including a cannula guide, lasers and deep brain stimulation (DBS) probes, etc.

Conformable Open Framework Headcoil

The following is a more detailed description of one of the preferred embodiments of the present invention. As shown in FIGS. 2A-5, and 7, one of the MRI coils 12 includes a MRI head coil (which will use reference number 12 for simplicity and clarity) having a framework 20 constructed of the previously described plurality of interconnecting primary support members 20a and secondary or medical implement support members 21. The interconnected primary and secondary support members, 20a and 21 respectively, are configured to conform to a patient's head, and to the head of essentially 100% of the patient population. The primary and secondary support members, 20a and 21 respectively, define an adjustable or pliable head coil system with a plurality of openings, including: anterior or face opening 30a, first side opening 30b, second side opening 30c, one or more posterior openings 30d, and crown opening 30e. Like with other embodiments, the framework 20 of the MRI head coil 12 provides support and comfort to a patient's head while also supporting or housing the MRI receiver antennae and/or imaging coils 40, and the diagnostic and surgical accessories 60 (such as for example, ultrasound transducers, and other sensors and medical devices such as electroencephalography EEG, electromyography EMG, electronystagmography ENG sensors, and the like). As discussed above, the MRI receiver antennae and/or imaging coils 40 can be connected to, enshrouded within, molded, or otherwise formed within the primary and/or secondary support members, 20a and 21 respectively,—e.g., sandwiched between two halves of the primary and secondary support members, 20a and 21 respectively.

The overall framework 20 construct, including the individual primary and secondary support members, 20a and 21 respectively, may be constructed in a shape or configuration to facilitate placement upon or around a patient during scanning, surgical, and/or therapeutic procedures. While not necessary with all MRI coils 12 of the present invention, the primary and secondary support members, 20a and 21 respectively, can have a generally flat inner surface that can be positioned against or proximate to a patient's skull or skin. The generally flat inner surface provides added comfort for the patient while the MRI head coil 12 is being worn. The outer surface of the primary and secondary support members, 20*a* and 21 respectively, can be generally rounded, arcuate, curvilinear, linear, angular, or they can take on a myriad of other shape configurations.

In addition, all or parts of the framework 20 can be, as mentioned above, constructed of a cell foam material (open or closed), a generally thin flexible band, or other acceptably adjustable and pliable materials such that the framework 20 is generally flexible and/or compressible to enable it to be selectively formed around a patient's head, and to facilitate the described connectivity and use.

Figure 2A:
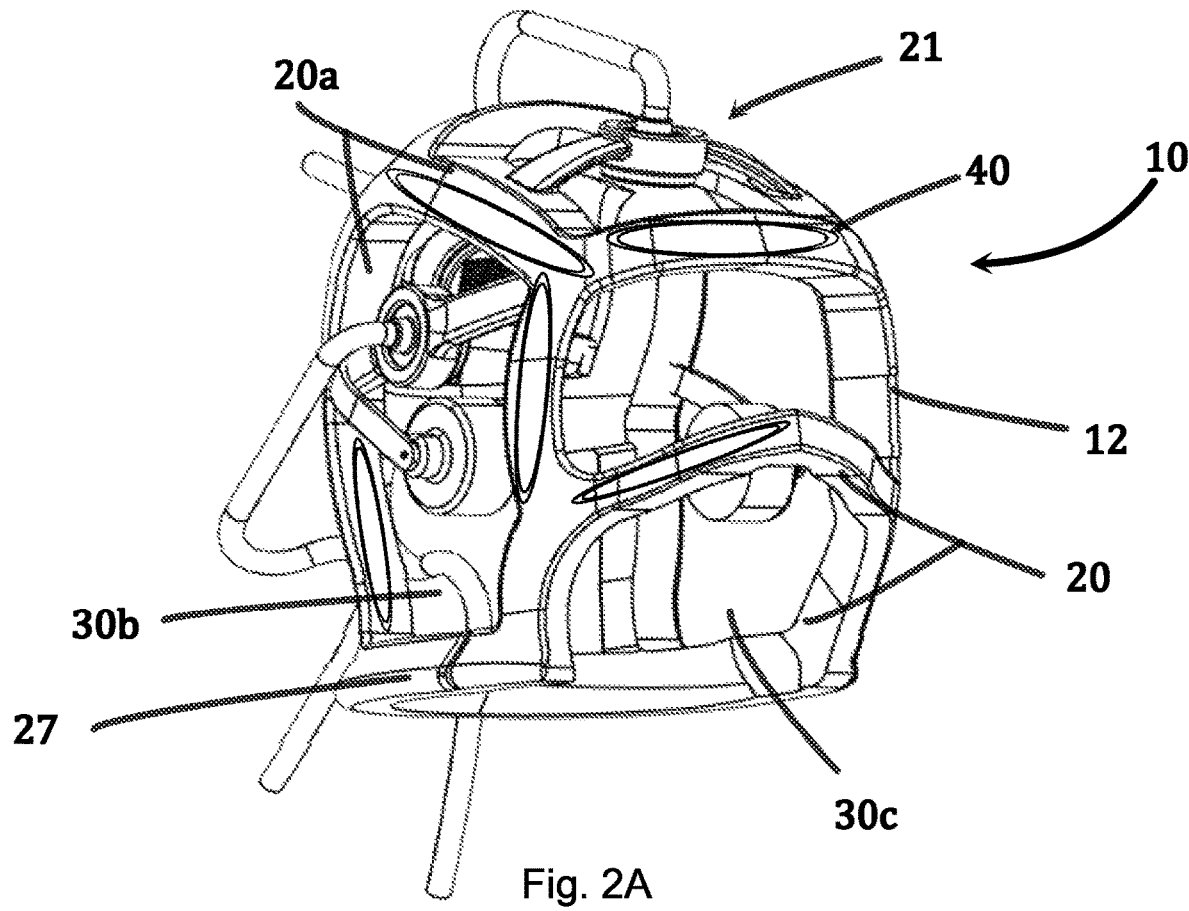
FIG. 2A is a front perspective view of an MRI head coil showing ultrasound, diagnostic, therapeutic, and/or interventional devices or therapy implements, according to an example embodiment of the present invention.
Figure 2B:
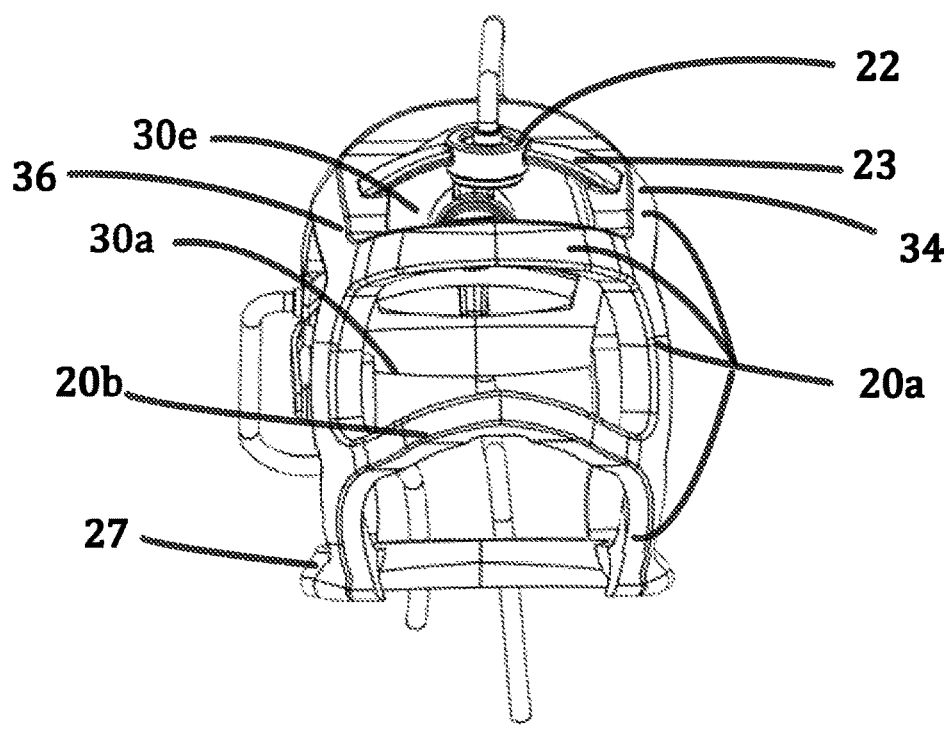
FIG. 2B is a front perspective view of an MRI head coil showing ultrasound, diagnostic, therapeutic, and/or interventional devices or therapy implements, according to an example embodiment of the present invention.
Figure 2C:
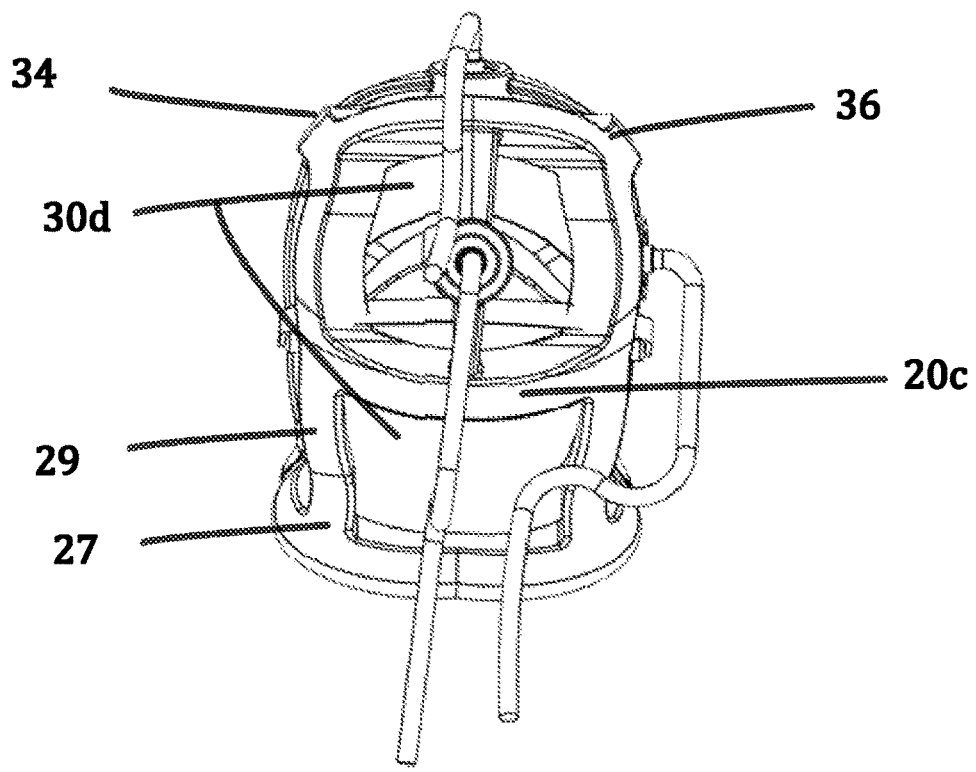
FIG. 2C is a top-rear perspective view of an MRI head coil showing ultrasound, diagnostic, therapeutic, and/or interventional devices or therapy implements, according to an example embodiment of the present invention.
Figure 2D:
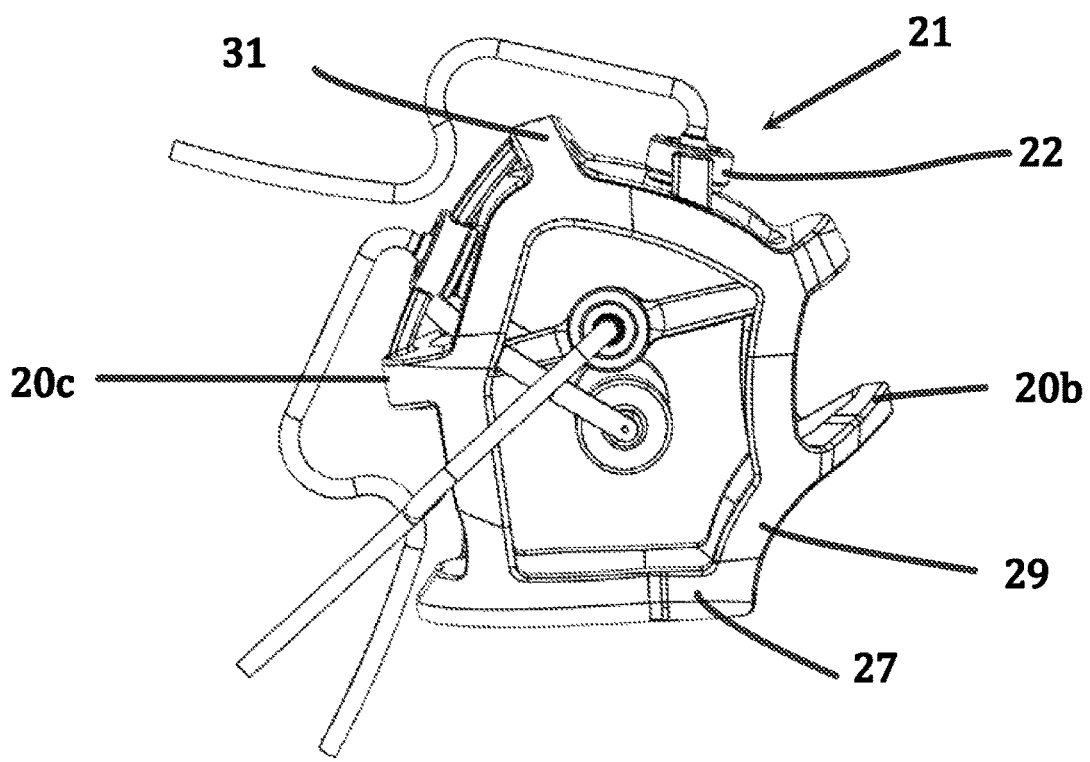
FIG. 2D is a first side view of an MRI head coil showing ultrasound, diagnostic, therapeutic, and/or interventional devices or therapy implements, according to an example embodiment of the present invention.
Figure 2E:
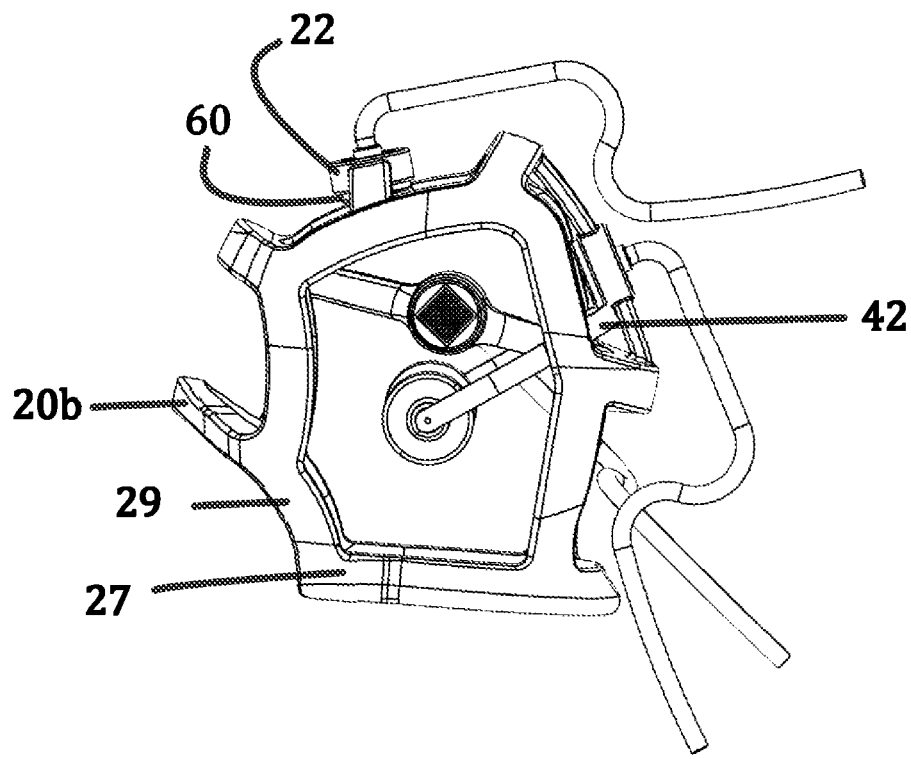
FIG. 2E is a second side view of an MRI head coil showing ultrasound, diagnostic, therapeutic, and/or interventional devices or therapy implements, according to an example embodiment of the present invention.
Figure 3:
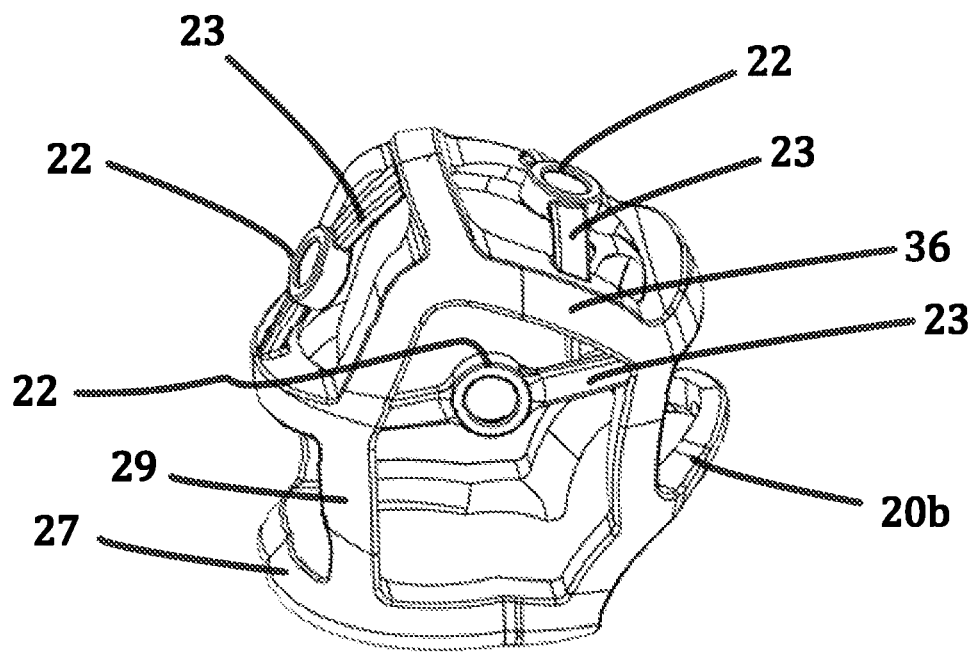
FIG. 3 is a side view of an MRI head coil showing ultrasound, diagnostic, therapeutic, and/or interventional devices or therapy implements, according to an example embodiment of the present invention.
Figure 4:
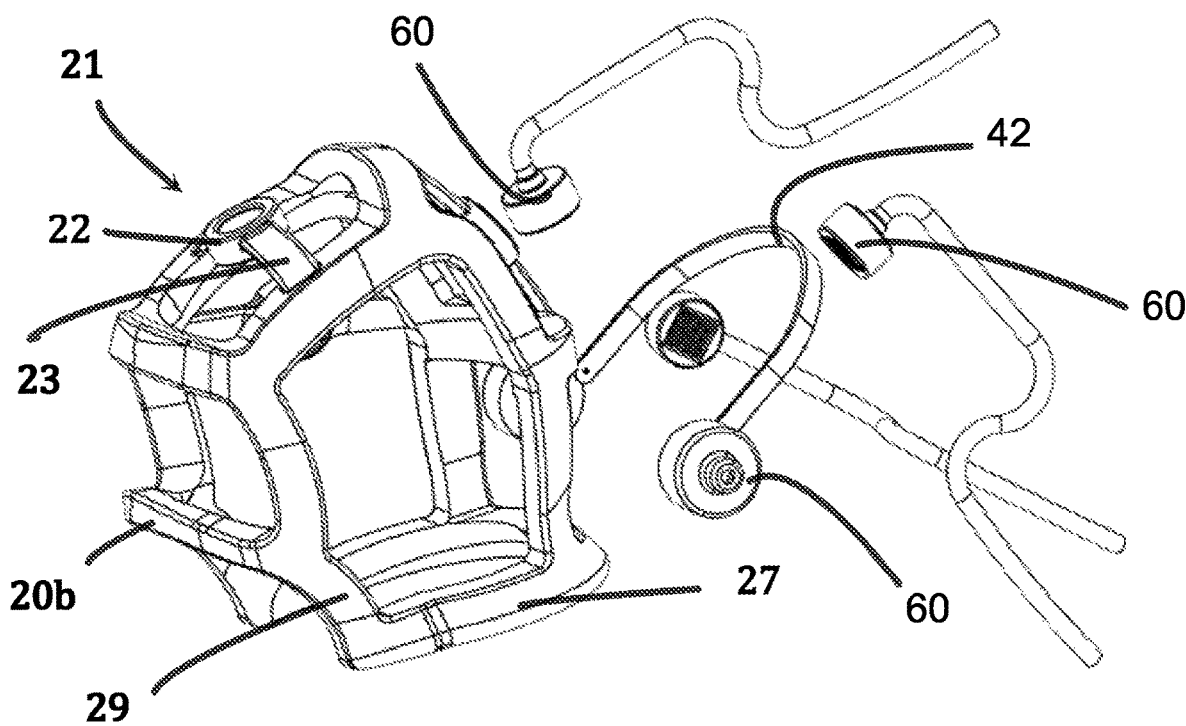
FIG. 4 is an exploded view of an MRI head coil showing ultrasound, diagnostic, therapeutic, and/or interventional devices or therapy implements, according to an example embodiment of the present invention.
Figure 5:
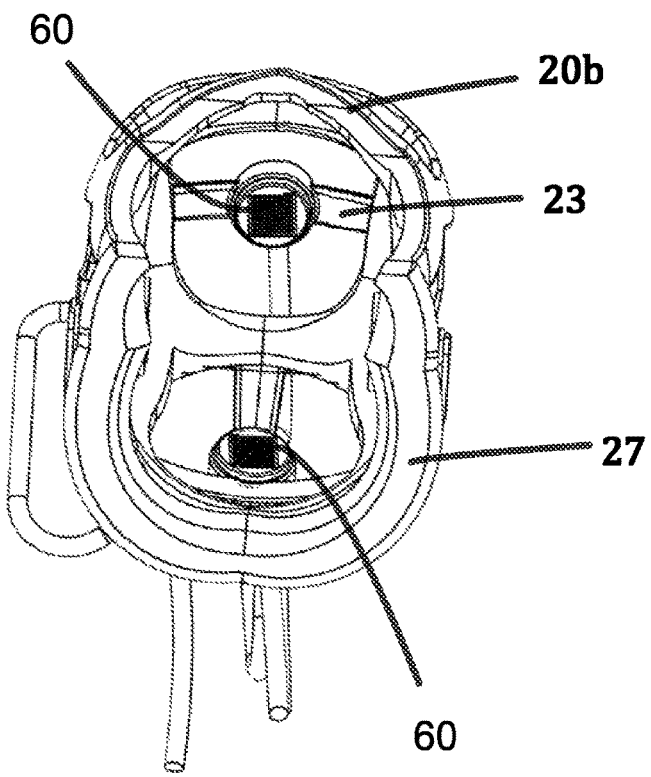
FIG. 5 is a bottom view of an MRI head coil showing ultrasound, diagnostic, therapeutic, and/or interventional devices or therapy implements, according to an example embodiment of the present invention.
Figure 6:
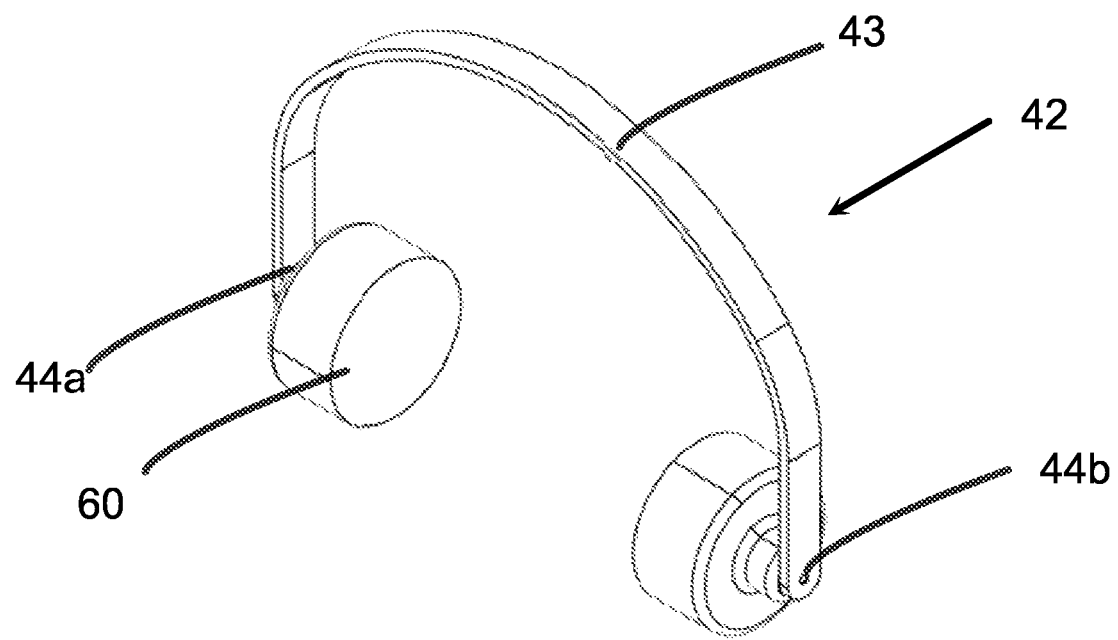
FIG. 6 is a perspective view of a diagnostic, therapeutic, and interventional device wearable with the MRI head coil, according to an example embodiment of the present invention.

As particularly illustrated in FIGS. 2A-3, the primary support members 20*a* of the conformable and open framework 20, include one or more base portions 27 that extend generally along the sides and around a back or posterior portion of a subject's head or neck. One or more generally upright portions 29 can extend generally upward from the base portions 27. A face member or portion 20*b* is provided that extends generally across a pair of upright portions 29 and may span across a portion of a subject's face when worn. Similarly, primary support members 20*a* may also include one or more rear portions 20*c* that can extend generally across a posterior portion of a subject's head when worn.

The primary support members 20*a* of the framework 20 may also include one or more crown portion 31 that can span across the crown of a subject's head and can be interconnected to a left portion 34 and a right portion 36, which also span generally proximate to the crown of a subject's head. Other portions or members of the plurality of primary support members 20*a* can be included within the framework 20 and can also include the MRI receiver antennae and/or imaging coils 40.

In one example embodiment of the open and conformable MRI head coil 12, the face member or portion 20*b* can have one or two free ends, or edges, such that it can be bent, flexed away from, or completely removed from the MRI head coil 12 and a subject or patient's head or face. The adjustability of the face member or portion 20*b* enables the MRI head coil 12 to be adjusted for patients with varying sized craniums. Its adjustability and removal also enable patients to feel less claustrophobic during a procedure. Fasteners, such as hook and loop fasteners can be used to secure ends of the face member or portion 20*b*, or even portions of other primary support members 20*a*, to a portion of the upright portions 29. It is envisioned that other fasteners and mechanisms can be employed to provide securement, such as snap features, temporary adhesives, clip or catch mechanisms, and the like.

It should be noted that, in at least one example embodiment, any of the primary support members 20*a*, or portions or members thereof, may be detachable or removable from the framework 20 of the MRI head coil 12. In this particular embodiment, contact or engagement surfaces can form a part of the MRI head coil 12 to enable continuity between the MRI receiver antennae and/or imaging coils 40, if needed, and communication with a hub and/or MRI scanning device or system. The contact or engagement surfaces can comprise any material that is capable of connecting ends or portions of the MRI receiver antennae or imaging coils 40 together and may be connected to, or formed as part of, the MRI head coil 12.

The adjustability of the embodiments of the MRI head coil 12 enable other medical devices and life supportive devices, such as ventilators, respirators, oxygen masks, tubes, catheters, electrodes, cervical collars, halos, probes, and other devices to be easily placed upon, or removed from, a patient. The ability to quickly and easily place or remove medical equipment while a patient undergoes diagnostic, therapeutic, and surgical procedures is a significant advantage over conventional birdcage head coils.

The openings 30*a*, 30*b*, 30*c*, 30*d* of the head coil 12 can act as ventilation and provide improved access to the subject or patient's head. The openings 30*a*, 30*b*, 30*c*, 30*d* can also provide access for surgical tools, frames, pins, and other mechanisms and devices used to stabilize a patient's anatomy during an interventional procedure, as further detailed herein. The openings 30*a*, 30*b*, 30*c*, 30*d* are also adapted to receive any device used during therapy, surgical, and interventional procedures, such as an ultrasound device (e.g., a LIFU or HIFU device). Side openings 30*b*, 30*c* can also provide mechanical communication with the patient's temples or ears for placement of ultrasound transducers and other medical devices or implements. The openings also provide access for the placement and removal of headphones, earbuds, or noise canceling headphones.

Again, while particular shapes, sizes, and locations of the openings 30*a*, 30*b*, 30*c*, 30*d* and primary support members 20*a* are depicted in the figures of the open framework 20, one skilled in the art will appreciate that the dimensions, shapes, and locations of the openings 30*a*, 30*b*, 30*c*, 30*d*, primary support members 20*a*, and any other depicted or described elements or members, can vary and may be selected and defined based upon typical therapy or surgical sites, tool sizes, device sizes, and the like.

As illustrated in FIGS. 2A, 2D, 4, and 6, the present invention includes an accessory device retention member 42 that is designed to hold one or more diagnostic or surgical accessory devices or implements 60 against the skull or skin of a patient being treated. As particularly, illustrated in FIG. 6, the accessory device retention member 42 can comprise a band 43 that can be curved or generally arcuate in shape. One or more diagnostic or surgical accessory devices or implements 60 can be coupled to or mounted on free ends 44*a* and 44*b* of the band 43 and arranged in a manner that enables them to be placed proximate to or flush against the skull or skin of the patient. The band 43 can have any length or is generally adjustable to accommodate patients of various sizes and shapes.

As briefly mentioned above, the MRI receiver coil system 10 of the various embodiments can include one or more diagnostic or surgical accessory devices or implements 60, such as ultrasound transducers (e.g., FUST transducers) mechanically integrated or coupled with the support assembly 20 and corresponding secondary support members 20*a*. This allows for the placement of diagnostic or surgical accessory devices 60, and the MRI receiver antennae or imaging coils 40, generally flush to the patient's skull or skin, at the same time, and generally in the same plane.

Further, diagnostic or surgical accessory devices or implements 60 can be repositioned in a myriad of locations on the patient's head due to the connectivity and attachment options of the framework 20. For instance, if the MRI receiver antennae and/or imaging coils 40 are interfering with the placement of the focused diagnostic or surgical accessory devices or implements 60, the flexibility of the primary and secondary support members, 20*a* and 21 respectively, the openings 30*a*, 30*b*, 30*c*, 30*d*, and the pliable MRI receiver antennae 40, permit and facilitates adaptive repositioning to allow for proper placement.

In an example embodiment of the present invention, the secondary support members 21 of the MRI head coil 12 provide support for the diagnostic or surgical accessory devices or implements 60. One or more of the secondary support members 21 is designed to hold or receive one or more diagnostic or surgical accessory devices or implements 60 and to position or hold the accessory device or implements 60 proximate to or flush against the patient's skull or skin. In one example embodiment, the secondary support members 21 comprise one or more hubs or housings or housing portions 22 that house or retain the diagnostic or surgical accessory devices or implements 60. The secondary support members 21 include one or more support arm portions 23 that are interconnected to and extend between portions of the framework 20 and a portion of the housing 22. The secondary support members 21 are positioned such that they extend into or between one or more of the openings 30a-30d.

The one or more support arm portions 23 can be manufactured from a generally pliable material that permits it to be adjustable or moveable within the space of the openings 30a-30d. The ability to adjust the one or more support arm portions 23 enables the accessory device or implements 60 to be moved or positioned in any location within or removed from the opening 30a-30d. The movement of the support arm portions 23 provide greater versatility in scanning or treatment locations.

Figure 7A:
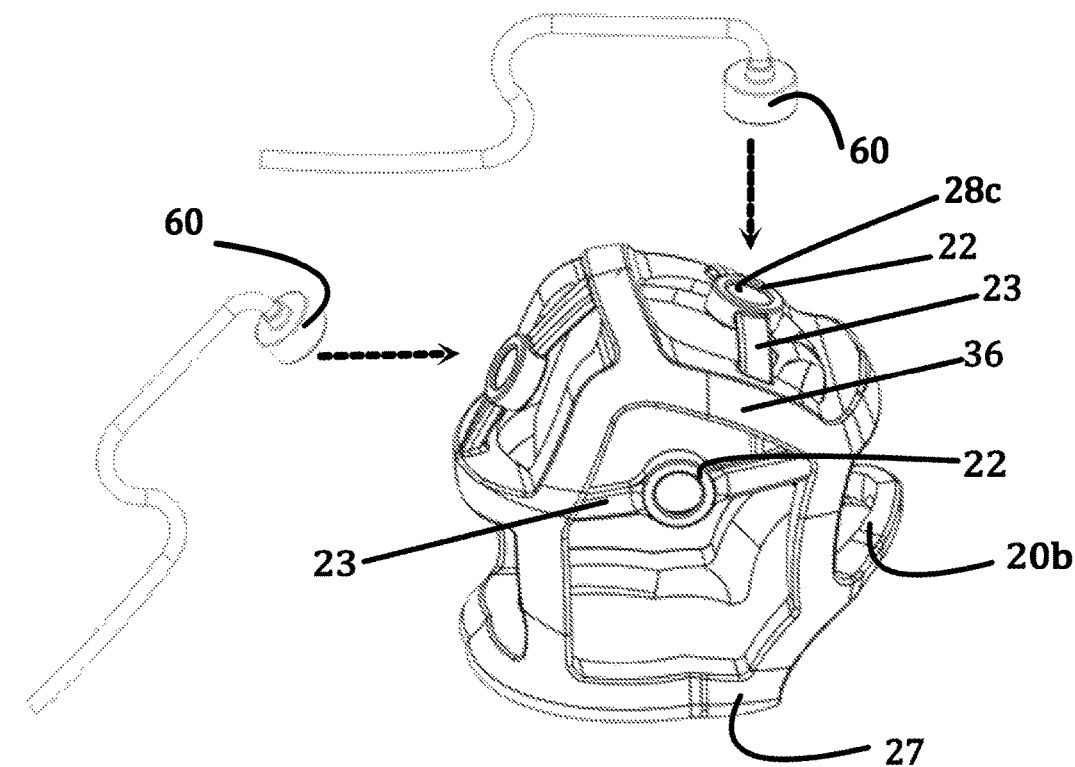
FIG. 7A is a side exploded view of an MRI head coil showing ultrasound, diagnostic, therapeutic, and/or interventional devices or therapy implements, according to an example embodiment of the present invention.
Figure 7B:
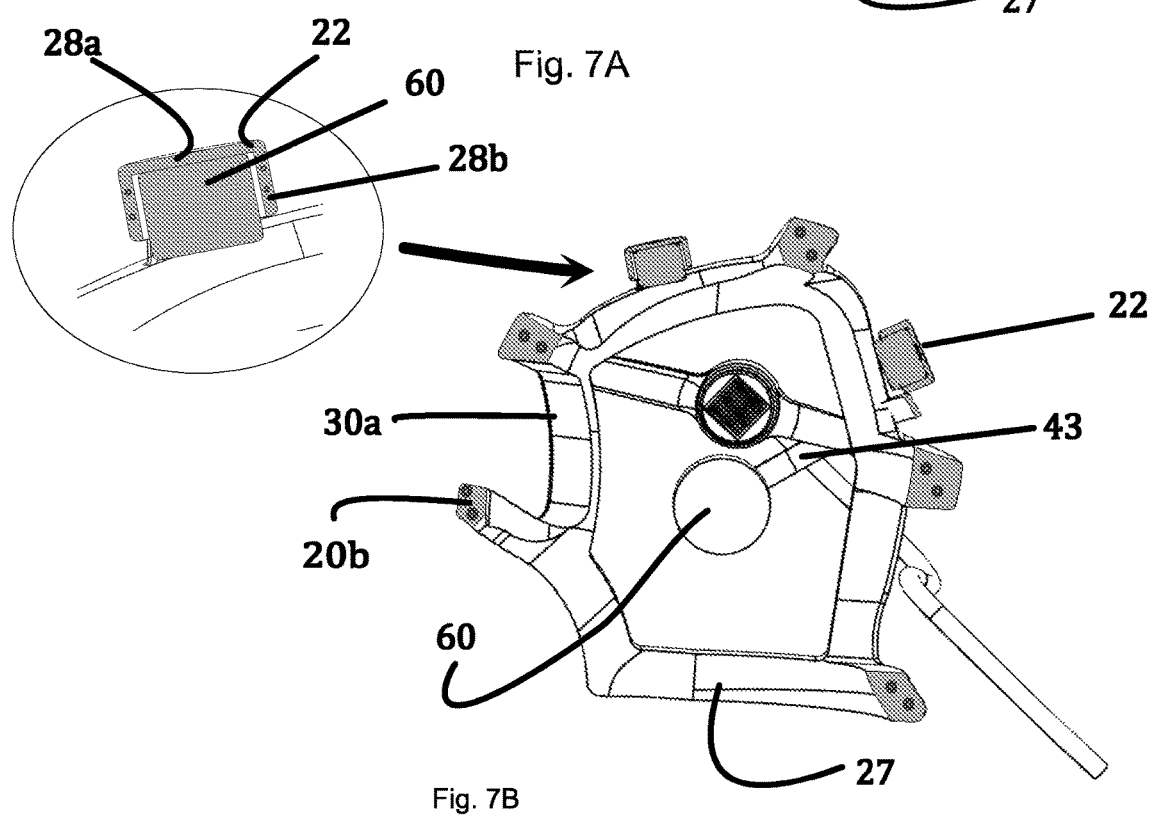
FIG. 7B is cross section of FIG. 2E illustrating the positioning of ultrasound, diagnostic, therapeutic, and/or interventional devices or therapy implements with respect to the MRI head coil, according to an example embodiment of the present invention.
Figure 8A:
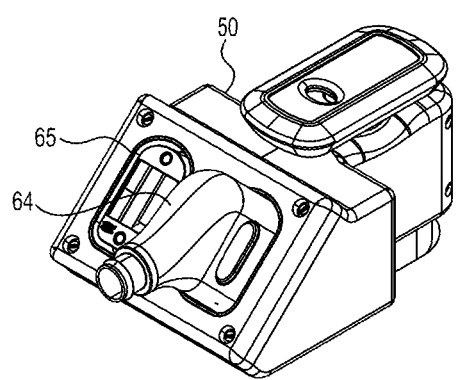
FIGS. 8A-8D are perspective views of a hub/preamp used for receiving and transmitting data between the wearable open and conformable MRI coil and an MRI scanner, according to an example embodiment of the present invention.
Figure 8B:
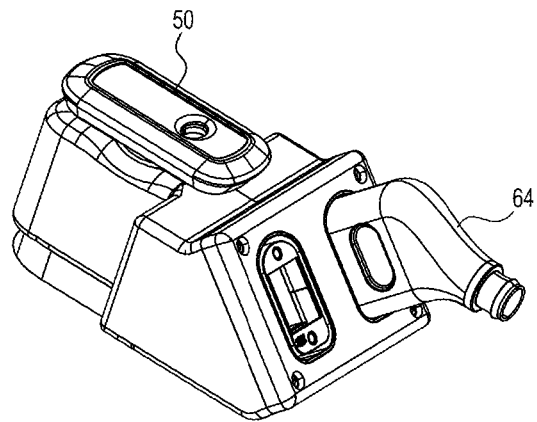
Figure 8C:
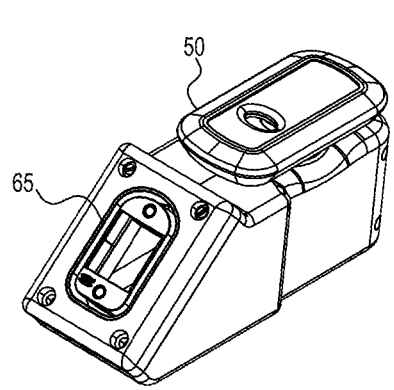
Figure 8D:
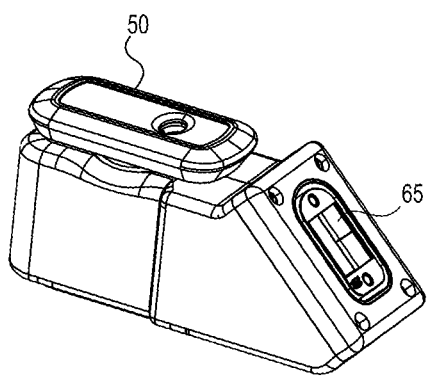

As illustrated in FIGS. 7A and 7B the housing 22, can comprise a base or top wall 28a and a peripheral wall 28b extending therefrom and defining an interior configured to receive one or more diagnostic or surgical accessory devices 60. In one example embodiment of the invention, the peripheral wall 28b of the housing 22 has a height generally less than a height or thickness of a diagnostic or surgical accessory device 60 to allow the accessory device 60 to extend beyond the height of the peripheral wall 28b and ensuring contact of the accessory device 60 with the skull or skin of the patient. The housing 22 can also comprise one or more openings or holes 28c extending through it to allow for passage of any wiring or cable extending from the accessory device 60.

As discussed above, one or more of the secondary support members 21 may include one or more MRI receiver antenna 40. The MRI receiver antenna 40 can extend through one or more of the support arm portions 23. In one embodiment of the invention, as particularly illustrated in FIG. 7B, the MRI receiver antenna 40 extends about and may be engaged within the peripheral wall of the housing 22 (see black dots in magnified view). As described above, having the MRI receiver antenna 40 extend through the support arm portions 23 and about the housing 22 of the secondary support members 21 permits imaging of the open areas 30a-30d and simultaneously imaging of the area with MRI and with a diagnostic or surgical accessory device 60. As illustrated in the figures, the secondary support members 21, housing 22, support arm portions 23 and any diagnostic or surgical accessory devices 60 can extend across any of the openings 30a, 30b, 30c, 30d. Further, they can extend in any direction across any of the openings 30a, 30b, 30c, 30d.

While the housing 22 is illustrated having a generally cylindrical shape, other shapes and configurations are also possible and should be considered to be within the spirit and scope of the present invention. The present invention also includes the ability to remove a housing 22 or a housing 22 and support arm portions 23 and replace it with another housing 22 and/or support arm portions 23 having a different size, shape, and/or configuration to accommodate a different diagnostic or surgical accessory devices 60.

When used for interventional or therapeutic procedures, the framework 20 is applied to the patient prior to adding fixation or other hardware and devices. The framework 20 and the configuration of the primary support members 20a, secondary support members, and openings 30a, 30b, 30c, 30d permits access to interventional hardware and test setups—e.g., cannula guides, head fixations, sterile draping, and the like. This, in turn, means that the framework 20 can interface with virtually all head fixation and connective devices. The framework 20, head fixation hardware, and interventional tools or devices can all touch the patient simultaneously with the MRI receiver antennae or imaging coils 40.

System Hub

The MRI receiver coil system 10 of the various embodiments of the present invention can also include a hub 50 that is able to receive or connect various MRI imaging coils 12, including the imaging coils of the MRI head coil 12. The MRI receiver antennae and/or imaging coils 40 of the MRI head coil 12 are bundled together into a plug or plugs 64 that connect to an external hub or preamp 50 (as illustrated in FIGS. 5A-5D) that interface or communicates with the MRI scanner. The hub 50 can have one or more sockets or receivers 52 to receive a number of different surface coil plugs, adapters, and the like. In one example embodiment of the invention, the hub 50 can accommodate any number of channels. For instance, 1 to 48 channels may be used that enable it to connect with the support assembly 20 and other imaging devices, such as a 24 cm surface coil, a 10 cm surface coil, a posterior surface coil, a spine surface coil, a face surface coil (discussed below), etc. The number of channels provided are merely exemplary and any number of channels are possible and are considered to be within the spirit and scope of the invention.

Although a particular shape, size, and location of openings 30a-30d are illustrated, one skilled in the art will appreciate that the number, dimensions and locations of openings 30a-30d may vary and may be selected based upon typical therapy or surgical sites, tool sizes, and the like. Therefore, the illustrations should not be considered limiting.

Sensor, Imaging and Imaging Coil Support

The framework 20 of the MRI coils 12 of any of the disclosed embodiments of the present invention can support or house the MRI receiver antennae or imaging coils 40, and other types of sensors and imaging devices. As described above, to capture the scanned images, the framework 20 supports or houses one or more MRI receiver or imaging coils 40. The MRI receiver antennae or imaging coils 40 receive the radio frequency signal from the patient and then transmit them to a connected MRI control system for processing and image generation. The MRI receiver antennae or imaging coils 40 may be fixed in, or removably attached to, an inner or outer surface of the framework 20. In one example embodiment, the MRI receiver antennae or imaging coils 40 can be connected to one or more fasteners fixed to the surface of the framework 20. The fasteners may comprise clips, snaps, hook and loop devices, adhesives, and the like.

As discussed above, the inner or outer surface of the framework 20 can include grooves or channels formed therein that receive and hold or retain the MRI receiver antennae or imaging coils 40. The MRI receiver or imaging coils 40 may be removable from the fasteners or grooves for repair, replacement, or to isolate or remove a particular portion or panel of the framework 20.

As particularly illustrated in FIG. 2A, the MRI receiver antennae and/or imaging coils 40 can also be molded, formed, housed, or positioned within the support assembly 20. For instance, during the manufacturing process, the support assembly 20 may be formed around the MRI receiver antennae and/or imaging coils 40. The framework 20 may also be 3D printed or thermal-formed around the MRI receiver antenna or imaging coils 40. The MRI receiver antenna and/or imaging coils 40 may also contain, or may be in communication with, a circuit board that can be attached to or imbedded within the framework 20.

The radiofrequency MRI receiver antennae and/or imaging coils 40 are comprised of a generally flexible material, such as a braided, stranded, or twisted wire, or other material capable of receiving radiofrequency signals, such as RF polymers. The flexibility of the MRI receiver antenna and/or imaging coils 40 enables portion of the MRI head coil 12 to be moved, bent or otherwise move without damaging the MRI receiver antenna and/or imaging coils 40.

The framework 20 of the MRI coil 12 is manufactured having a thickness that positions the MRI receiver antennae or imaging coils 40 at the skin surface of a patient or at a predefined distance from a patient's skin. In one embodiment, the framework 20 has a thickness to position the MRI receiver antennae and/or imaging coils 40 either flush against, or a distance of approximately 5 mm from, the surface or skin of the patient. The distance of the MRI receiver antennae and/or imaging coils 40 is designed to have a high signal-to-noise ratio, while still being safe for the patient. Greater or lesser MRI frequencies and/or MRI field strengths are possible and should be considered to be within the spirit and scope of the present invention. Additionally, RF polymers, which may be proven to be safe for patients, may be conformed to the head with little or no foamed structure.

In an example embodiment of the invention, for instance, the MRI receiver antennae and/or imaging coils 40 may be underlapped. The underlapping of the MRI receiver antennae and/or imaging coils 40 may occur in some or all of the MRI receiver antennae and/or imaging coils 40. The framework 20 MRI receiver antennae and/or imaging coils 40 can have six (6) channels, although the number of channels may be increased or decreased depending upon the particular need and application.

Figure 9:
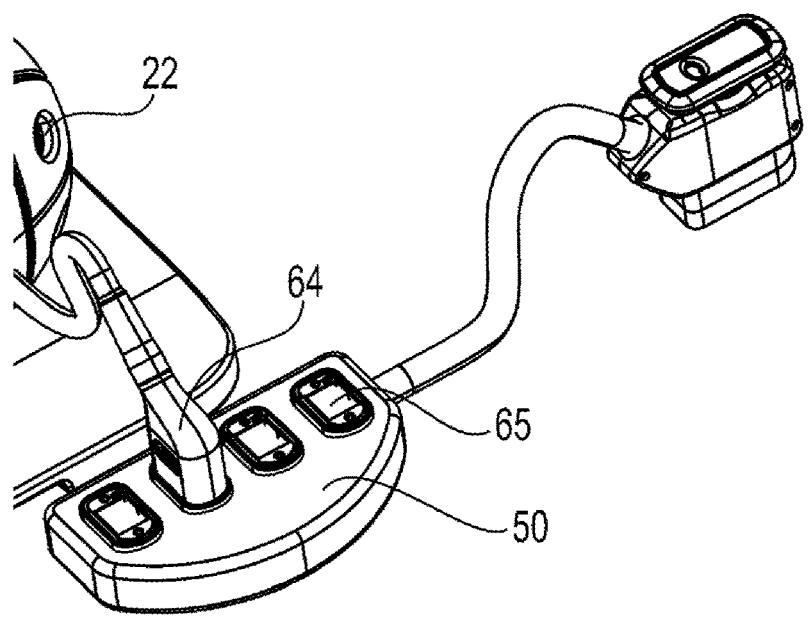
FIG. 9 is a perspective view of a hub/preamp used for receiving and transmitting data between the MRI coil and an MRI scanner, according to an example embodiment of the present invention
Figure 10A:
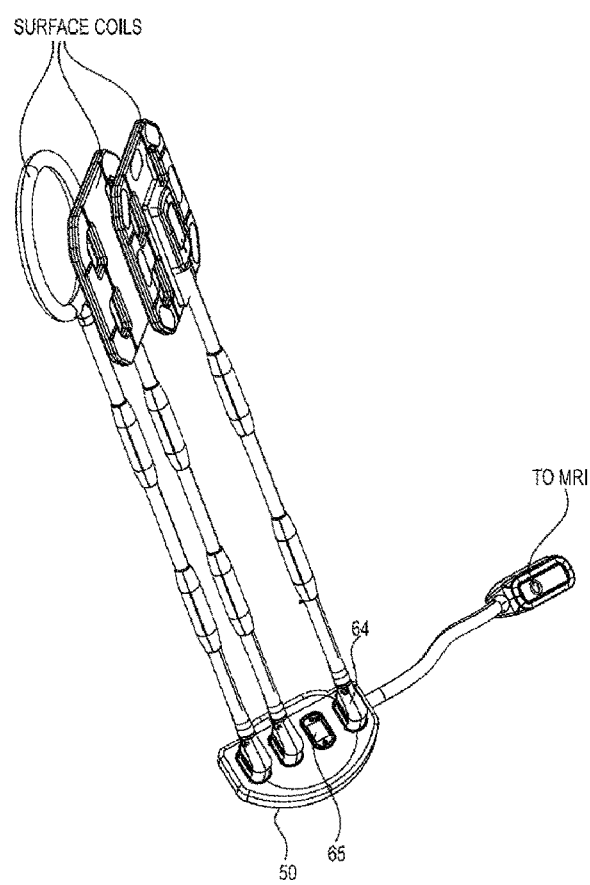
FIG. 10A is a perspective view of a preamp (signal amplifier) assembly having a plurality of connectors for connecting distinct MRI coils, according to an example embodiment of the present invention.
Figure 10B:
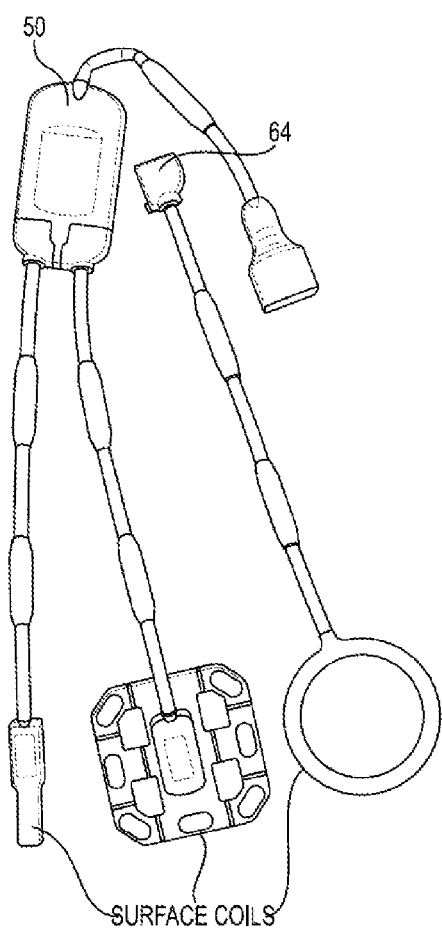
FIG. 10B is a top view of a preamp assembly having distinct MRI coils, according to an example embodiment of the present invention.

The MRI receiver antennae and/or imaging coils 40 and/or the accessory devices or implements 60 can be operatively coupled together by, for instance, plugging into a hub that is then connected to a receptacle 65 of preamp (signal amplifier) 50. Various plug or connection configurations are possible and should be considered to be within the spirit and scope of the invention. Although FIGS. 9 and 10A-10B illustrate surface coils and MRI imaging coils being connected to the preamp (signal amplifier) 50, it should be understood that any number of surface coils, MRI imaging coils, or MRI coils 12 of the present invention may be connected to the preamp 50.

The preamp (signal amplifier) 50 can also receive other devices or surface coils to expand the capabilities of the MRI receiver coil system 10. For example, the adjustable or pliable framework 20 of a surface coil assembly of a head unit may include a face surface coil or a chin surface coil, each having a number of channels. For instance, the face and chin surface coils and can each have at least 2 to 6 channels that are used to image the anterior aspects of a patient's head. The face and chin surface coils may also have more than 6 channels. The face surface coil includes a support or base that is removably connectable or positionable proximate the framework 20. The face or chin surface coils also include one or more MRI receiver antennae and/or imaging coils 40 that are connected to, and are in communication with, the preamp 50. The face surface coil may include one or more holes or openings that permit a user or patient to more easily breathe and speak while undergoing a procedure.

The open and conformable framework 20 may also include one or more sensors operatively coupled to, or positionable with respect to, the framework 20. The sensors may comprise electroencephalography EEG, electromyography EMG, or electronystagmography ENG sensors, although other sensors may also be used. In one embodiment, an inner surface of framework 20 may have indicia or marks that may identify a sensor's location. The indicia enables a practitioner to easily identify and place the sensors, and to relocate them in exact positions for later diagnostic, therapeutic, or interventional procedures.

In another embodiment, sensor fasteners may be connected to the inner surface of the framework 20 of the MRI coil 12. The sensor fasteners may comprise snap fasteners, or other fasteners described herein, that can be used with electroencephalography EEG, electromyography EMG, or electronystagmography ENG sensors. The openings or panels permit cables attached to the sensor to be passed through the framework 20 and connected to their consoles.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An open and conformable MRI head coil system that is configured to simultaneously perform MRI imaging and another medical procedure, the system being wearable about and able to be in contact with a head of a patient, the system comprising:
    an MRI head coil comprising a plurality of interconnected primary support members creating an open framework defining one or more openings;
    one or more MRI receiver antennae being associated with one or more of the plurality of interconnected primary support members and contactable to the head of the patient;
    at least one implement support member, the implement support member extending at least partially across an opening amongst the one or more openings and the implement support member comprising a housing to at least partially contain an ultrasound transducer, the housing comprising a hole for passage of cabling to the ultrasound transducer; and
    wherein the MRI head coil system is configured to position the one or more MRI receiver antennae and the ultrasound transducer flush with a skull of the patient.

2. The system of claim 1, wherein the one or more MRI receiver antennae are contained within one or more of the plurality of interconnected primary support members.

3. The system of claim 1, wherein the plurality of interconnected primary support members and the at least one implement support member are constructed of a pliable material.

4. The system of claim 1, further comprising the ultrasound transducer.

5. The system of claim 1, wherein the housing has a base wall and a peripheral wall defining an interior and the peripheral wall having a height generally less than a thickness of the ultrasound transducer.

6. The system of claim 1, wherein at least one of the housing or the implement support member, or both, are removable to accommodate different sizes or shapes of ultrasound transducers.

7. The system of claim 1, wherein the housing comprises an elastic material stretchable about a portion of the ultrasound transducer.

8. The system of claim 1, further comprising an ultrasound transducer retainer having one or more end portions adapted to receive at least one ultrasound transducer.

9. The system of claim 8, wherein the retainer comprises at least a pair of end portions, each being adapted to receive at least one ultrasound transducer.

10. The system of claim 1, further including one or more interventional or fixation devices configured to be in contact with the head of the patient simultaneously with the one or more MRI receiver antennae and the at least one ultrasound transducer.

11. A wearable MRI imaging system that is conformable to a head of a patient for simultaneously holding one or more MRI receiver antennae and one or more medical implements flush against a skin of a patient, the system comprising:
   a conformable MRI head coil configured to be worn on a head of a patient, the MRI head coil having an open and pliable framework housing one or more MRI receiver antennae that are positionable flush against the skin of the patient, the framework defining one or more access openings configured to provide access to the head;
   one or more medical implements disposed between a portion of the framework and the skin of the patient; and
   one or more pliable implement support members extending at least partially across at least one of the openings, the one or more medical implements being disposed between the patient's skin and one or more of the implement support members, the implement support member coupled with or comprising a housing portion that is removable to accommodate different sizes or shapes of medical implements using different housing portions;
   wherein the MRI head coil system is configured to position the MRI receiver antennae and the one or more medical implements flush against the skin of the patient.

12. The system of claim 11, wherein the framework of the MRI head coil comprises a plurality of primary pliable support members, the one or more MRI receiver antennae being enshrouded within one or more of the plurality of pliable primary support members such that the MRI receiver antennae are positionable flush with a surface of the head of the patient when worn.

13. The system of claim 11, wherein the housing portion defines an interior and at least one arm extending between the housing portion and a portion of the framework.

14. The system of claim 13, wherein the housing portion comprises a base wall and a peripheral wall defining the interior and the peripheral wall having a height generally less than a thickness of the medical implements.

15. The system of claim 14, wherein the base wall of the housing portion includes an opening extending through it to permit passage of at least a portion of the medical implement.

16. The system of claim 13, wherein the housing portion comprises an elastic material stretchable about a portion of a medical implement amongst the one or more medical implements.

17. The system of claim 11, further comprising one or more sensors attachable framework, the one or more sensors configured to monitor one or more physiological characteristics.

18. The system of claim 11, further comprising one or more interventional or fixation devices configured to be in contact with a patient simultaneously with the one or more MRI receiver antennae and the one or more medical implements.

19. The system of claim 11, wherein the one or more medical implements comprises an ultrasound transducer.

20. The system of claim 11, wherein the system is configured to perform an MRI imaging and operation of the one or more medical implements simultaneously.

* * * * *